(12) United States Patent
Okawa et al.

(10) Patent No.: US 9,876,974 B2
(45) Date of Patent: Jan. 23, 2018

(54) ENDOSCOPE

(71) Applicant: OLYMPUS CORPORATION, Tokyo (JP)

(72) Inventors: Fumiyuki Okawa, Tama (JP); Hidenori Hashimoto, Sagamihara (JP); Yasunori Matsui, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/371,676

(22) Filed: Dec. 7, 2016

(65) Prior Publication Data
US 2017/0085825 A1  Mar. 23, 2017

Related U.S. Application Data (63) Continuation of application No. PCT/JP2015/075518, filed on Sep. 8, 2015.

(30) Foreign Application Priority Data

Dec. 4, 2014  (JP) .................................. 2014-246136

(51) Int. Cl.
*H04N 7/18*   (2006.01)
*H04N 11/02*  (2006.01)
(Continued)

(52) U.S. Cl.
CPC ..... *H04N 5/37455* (2013.01); *A61B 1/00009* (2013.01); *A61B 1/00112* (2013.01);
(Continued)

(58) Field of Classification Search
None
See application file for complete search history.

(56) References Cited

U.S. PATENT DOCUMENTS

| 4,788,981 | A  | * | 12/1988 | Nagasaki | ................. | A61B 8/00 310/334 |
|---|---|---|---|---|---|---|
| 6,383,183 | B1 | * | 5/2002 | Sekino | ............... | A61B 18/1206 606/34 |
| 2003/0122926 | A1 | * | 7/2003 | Kumei | ................. | H04N 5/2254 348/65 |
| 2004/0019351 | A1 | * | 1/2004 | Ohyama | .............. | A61B 18/149 606/46 |

(Continued)

FOREIGN PATENT DOCUMENTS

| CN | 102970914 A | 3/2013 |
|---|---|---|
| EP | 2567652 A1 | 3/2013 |

(Continued)

OTHER PUBLICATIONS

International Search Report dated Dec. 15, 2015 issued in PCT/JP2015/075518.

(Continued)

*Primary Examiner* — Talha M Nawaz
(74) *Attorney, Agent, or Firm* — Scully, Scott, Murphy & Presser, P.C.

(57) ABSTRACT

An endoscope is an endoscope connectable to a processor provided with a high frequency component enhancement circuit configured to perform, for an image pickup signal having an attenuated high frequency component, enhancement correction of the high frequency component, the endoscope including: a CMOS image sensor provided with an image pickup portion configured to pick up an optical image of a subject and generate an analog image pickup signal and an A/D converting portion configured to convert the analog image pickup signal to a digital image pickup signal and output the digital image pickup signal; a cable for transmitting the digital image pickup signal; and a filter having frequency characteristics equalizing frequency characteristics of the high frequency component enhancement circuit.

3 Claims, 12 Drawing Sheets

(51) Int. Cl.

| | | |
|---|---|---|
| *H04N 9/47* | (2006.01) | |
| *H04N 5/3745* | (2011.01) | |
| *A61B 1/04* | (2006.01) | |
| *A61B 1/00* | (2006.01) | |
| *A61B 1/05* | (2006.01) | |
| *G02B 23/24* | (2006.01) | |
| *G06T 5/20* | (2006.01) | |
| *H04N 5/225* | (2006.01) | |
| *H04N 5/268* | (2006.01) | |
| *H04N 7/10* | (2006.01) | |

(52) U.S. Cl.
 CPC ................. *A61B 1/04* (2013.01); *A61B 1/05* (2013.01); *G02B 23/2484* (2013.01); *G06T 5/20* (2013.01); *H04N 5/2253* (2013.01); *H04N 5/268* (2013.01); *H04N 7/10* (2013.01); *H04N 7/183* (2013.01); *H04N 2005/2255* (2013.01)

(56) References Cited

U.S. PATENT DOCUMENTS

2010/0033730 A1\* 2/2010 Kim .................. G01B 9/02004
 356/479
2013/0041220 A1\* 2/2013 Kutsuma ........... A61B 1/00009
 600/109

FOREIGN PATENT DOCUMENTS

| JP | 2001-028709 A | 1/2001 |
|---|---|---|
| JP | 2012-115531 A | 6/2012 |
| JP | 2013-094269 A | 5/2013 |
| WO | WO 2012/017735 A1 | 2/2012 |

OTHER PUBLICATIONS

Japanese Office Action dated May 10, 2016 issued in Japanese Patent Application No. 2016-506918.

\* cited by examiner

ENDOSCOPE

CROSS REFERENCE TO RELATED APPLICATION

This application is a continuation application of PCT/JP2015/075518 filed on Sep. 8, 2015 and claims benefit of Japanese Application No. 2014-246136 filed in Japan on Dec. 4, 2014, the entire contents of which are incorporated herein by this reference.

BACKGROUND OF THE INVENTION

1. Field of the Invention

The present invention relates to an endoscope mounted with an image pickup device configured to output a digital signal as an image pickup signal.

2. Description of the Related Art

Conventionally, an endoscope provided with an image pickup device has been widely used in a medical field and an industrial field. Further, a technique of configuring an endoscope system in which a signal processing apparatus referred to as a processor and attachably and detachably connected to an endoscope is responsible for various signal processing related to the endoscope is also known.

Further, recently, there is a tendency that, in an endoscope adopting a CCD image sensor as an image pickup device, the number of pixels of the CCD image sensor increases. In an endoscope of this kind, further faster processing is required than conventionally required as the number of pixels increases.

In an endoscope of this kind, it is difficult to appropriately transmit a signal output from the CCD image sensor arranged at a distal end of an insertion portion of the endoscope because of reasons that a cable connecting the image pickup device arranged on a distal end portion and the processor is relatively long, that a diameter of the cable is restricted in order to realize reduction in a diameter of the insertion portion of the endoscope, and so on.

In view of the above situation, a system has been also disclosed recently in which CDS processing (correlated double sampling) is performed for an image pickup signal of the CCD image sensor on the distal end portion of the endoscope to transmit the image pickup signal via the cable after reducing a frequency band of the signal, while the frequency deterioration in the cable is corrected by a predetermined analog circuit (an enhancement circuit or the like) arranged in the receiving-side processor or the like (see Japanese Patent Application Laid-Open Publication No. 2012-115531).

Note that, though the technique disclosed in Japanese Patent Application Laid-Open Publication No. 2012-115531 is such that corrects a frequency component, a technique of digitally correcting a frequency-deteriorated component is also known.

On the other hand, recently, an endoscope adopting a CMOS image sensor as an image pickup device has been also proposed.

A CMOS image sensor of this kind is provided with an A/D converting portion together with an image pickup portion in its sensor chip. An output signal as a sensor is a digital signal.

Here, from a viewpoint of frequency characteristics, transmission of a digital signal is not easily influenced by physical characteristics of a cable itself in comparison with transmission of an analog signal. Therefore, since an endoscope adopting a CMOS image sensor of this kind outputs a sensor output signal as a digital signal, image quality is influenced little by signal deterioration even in the case of signal transmission with a relatively long cable, in comparison with an endoscope adopting a CCD image sensor configured to output a sensor output signal as an analog signal.

SUMMARY OF THE INVENTION

An endoscope of an aspect of the present invention is an endoscope connectable to a first processor provided with a high frequency component enhancement circuit for performing, for an image pickup signal having an attenuated high frequency component, enhancement correction of the high frequency component, the endoscope including: an insertion portion to be inserted into a subject; an image pickup device provided at a distal end of the insertion portion and provided with an image pickup portion configured to pick up an optical image of the subject and generate an analog image pickup signal and an A/D converting portion configured to convert the analog image pickup signal to a digital image pickup signal and output the digital image pickup signal; a cable having one end connected to the image pickup device, the cable being for transmitting the digital image pickup signal to another end side; and an inverse characteristic filter provided at the other end of the cable and having frequency characteristics equalizing frequency characteristics of the high frequency component enhancement circuit.

DETAILED DESCRIPTION OF THE PREFERRED EMBODIMENT(S)

Embodiments of the present invention will be described below with reference to drawings.

Figure 1:
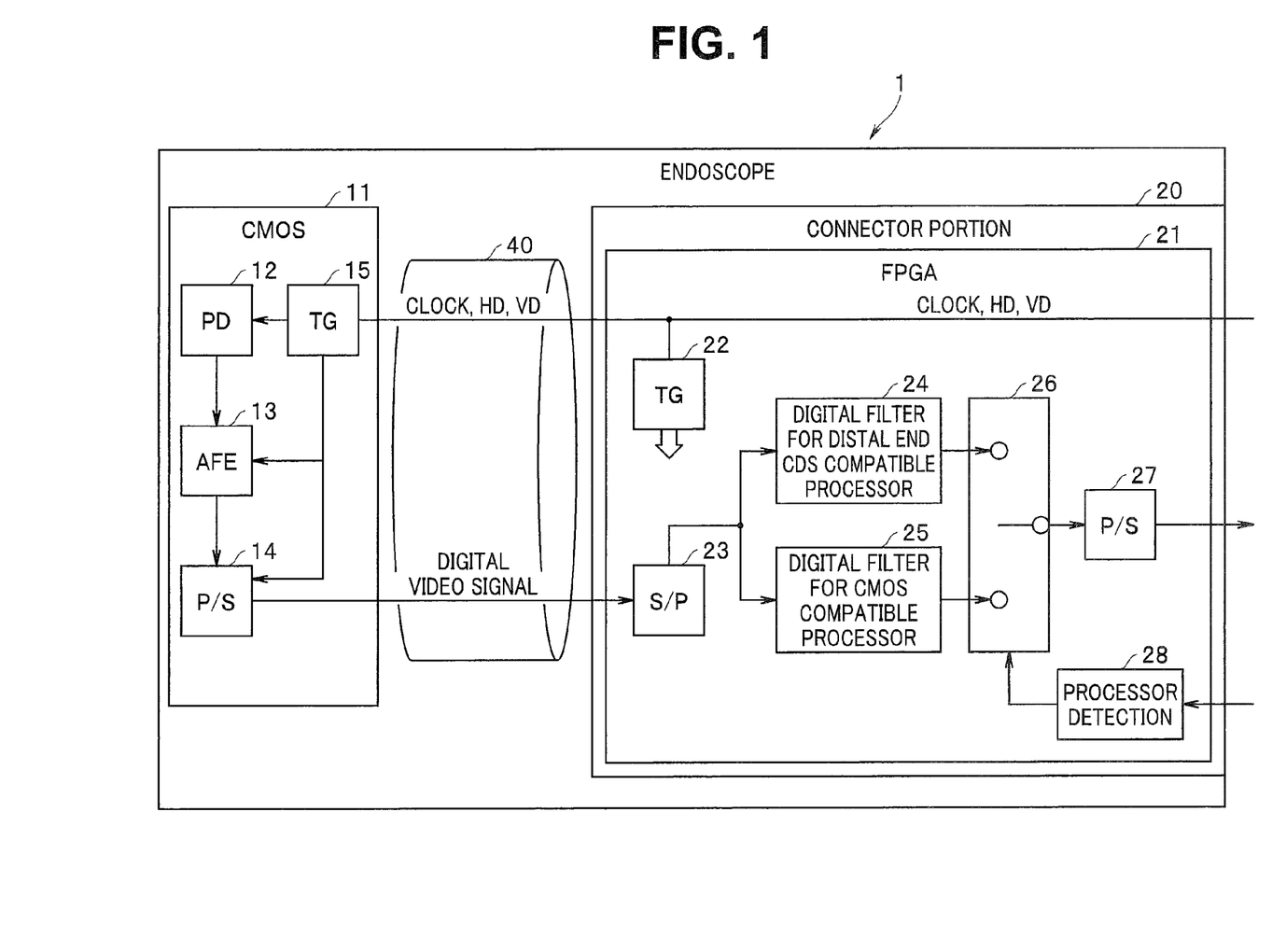
FIG. 1 is a diagram showing a configuration of an endoscope of a first embodiment of the present invention.

As shown in FIG. 1, an endoscope 1, which is a first embodiment of the present invention, is provided with a CMOS image sensor 11 provided at a distal end of an insertion portion to be inserted into a subject and configured to pick up an optical image of the subject and output a predetermined digital image pickup signal; a cable 40 connected to the CMOS image sensor 11 and configured to transmit the digital image pickup signal; and a connector portion 20 connected to a processor as a signal processing apparatus configured to perform predetermined signal processing (details are to be described later).

The CMOS image sensor 11 is configured including: a timing generator (TG) 15 configured to generate a clock signal, a horizontal synchronization signal HD and a vertical synchronization signal VD fitted to operation specifications of the CMOS image sensor 11 and pulses for various signal processing, based on a predetermined clock signal and synchronization signals HD, VD transmitted from a clock synchronization signal generation circuit 31 (see FIG. 5) of a processor 3; an image pickup portion 12 (PD 12) configured to pick up an optical image of a subject and generate a predetermined analog image pickup signal, by the clock signal, the horizontal synchronization signal HD and the vertical synchronization signal VD generated by the timing generator 15; an AFE circuit 13 is configured to perform predetermined signal processing for the analog image pickup signal and provided with an A/D converting portion which converts the analog image pickup signal to a digital image pickup signal and output the digital image pickup signal; and a P/S circuit 14 configured to perform parallel/serial conversion of the digital image pickup signal from the AFE circuit 13 and output the signal to a subsequent stage.

The cable 40 transmits the predetermined clock signal and the synchronization signals HD, VD transmitted from the processor 3 to the CMOS image sensor 11, and transmits the digital image pickup signal, which is a serial signal obtained by parallel/serial conversion by the P/S circuit 14, to an S/P conversion circuit 23 provided inside the connector portion 20.

In the present embodiment, a circuit for performing predetermined signal processing for the digital image pickup signal is configured with an FPGA (hereinafter referred to as the FPGA 21) inside the connector portion 20.

Receiving the clock signal and the synchronization signals HD, VD generated by the processor 3, the FPGA 21 outputs the signals to the CMOS image sensor 11.

On the other hand, the FPGA 21 is provided with: a timing generator (TG) 22 configured to generate pulses for various signal processing based on the clock signal generated in the processor 3; the S/P conversion circuit 23 configured to perform serial/parallel conversion of the digital image pickup signal, which is the serial signal, outputted from the CMOS image sensor 11; a digital filter for distal end CDS compatible processor 24 (hereinafter referred to as the CDS compatible digital filter 24) connected to the S/P conversion circuit 23; and a digital filter for CMOS compatible processor 25 (hereinafter referred to as the CMOS compatible digital filter 25) similarly connected to the S/P conversion circuit 23.

Here, the CDS compatible digital filter 24 is configured as an inverse characteristic filter having characteristics of equalizing frequency characteristics of an enhancement circuit for distal end CDS 33 (details are to be described later) in the processor 3. The CDS compatible digital filter 24 is adapted to effectively work when the endoscope 1 mounted with the CMOS image sensor 11 is connected to the processor 3 including the enhancement circuit 33.

On the other hand, the CMOS compatible digital filter 25 is configured as a filter having characteristics different from those of the CDS compatible digital filter 24. The CMOS compatible digital filter 25 is adapted to effectively work when the endoscope 1 mounted with the CMOS image sensor 11 is connected to a processor 3A which is not provided with the enhancement circuit 33 and configured to perform processing appropriate for the CMOS image sensor 11.

Returning to FIG. 1, the FPGA 21 is further provided with: a signal route switching portion 26 configured to switch an output signal route between the CDS compatible digital filter 24 and the CMOS compatible digital filter 25; a P/S circuit 27 configured to perform parallel/serial conversion of an output signal from the signal route switching portion 26 and output the output signal to the processor 3; and a processor detection circuit 28 configured to switch the signal route in the signal route switching portion 26 according to a classification of a processor connected to the endoscope 1.

Figure 2:
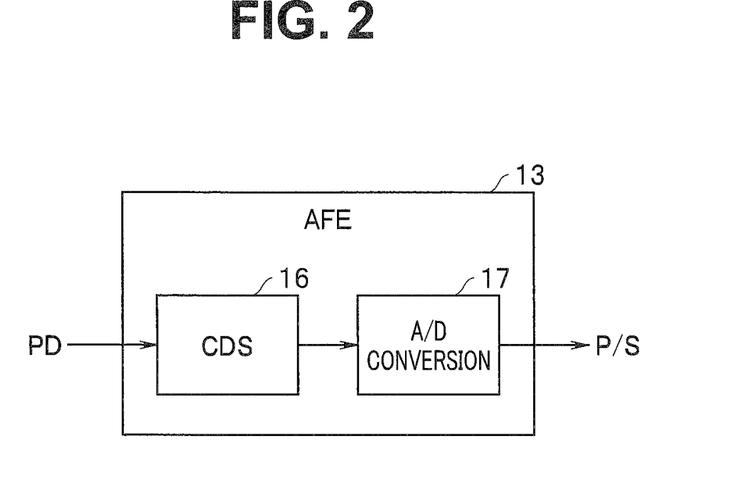
FIG. 2 is a diagram showing a configuration of an AFE circuit in a CMOS in the endoscope of the first embodiment.

Note that, as shown in FIG. 2, the AFE circuit 13 is configured being provided with a CDS circuit 16 configured to perform predetermined correlated double sampling processing for an analog image pickup signal from the image pickup portion 12 and an A/D conversion circuit 17 configured to perform A/D conversion of the analog image pickup signal for which the correlated double sampling processing has been performed and output the resultant digital signal.

Next, the processor 3 and the processor 3A to which the endoscope 1 can be connected will be described in detail.

Figure 3:
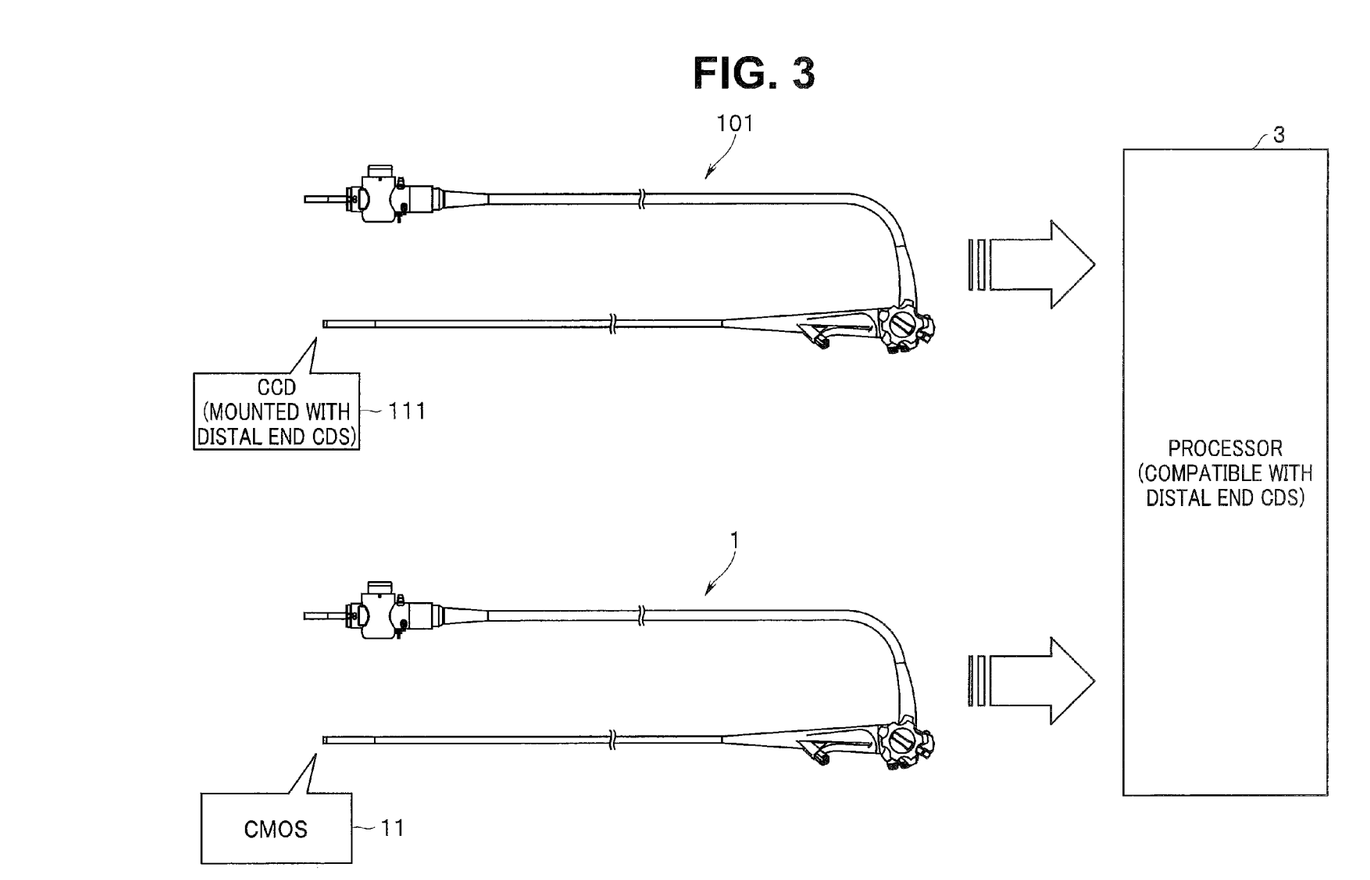
FIG. 3 is a diagram showing a connection relationship among the endoscope of the first embodiment, a conventional endoscope and a distal end CDS compatible processor.

FIG. 3 is a diagram showing a connection relationship among the endoscope of the present embodiment, a conventional endoscope and the distal end CDS compatible processor (the processor 3).

As shown in FIG. 3, the processor 3 is a distal end CDS compatible processor connectable to a conventional endoscope 101 provided with a circuit for performing CDS processing together with a CCD image sensor on a distal end portion of the endoscope. On the other hand, even in a case of an endoscope adopting a CMOS image sensor, the processor 3 can perform appropriate image signal processing in the processor if the endoscope is the endoscope 1 configured as in the present embodiment described above, when the endoscope is connected to the processor.

Figure 5:
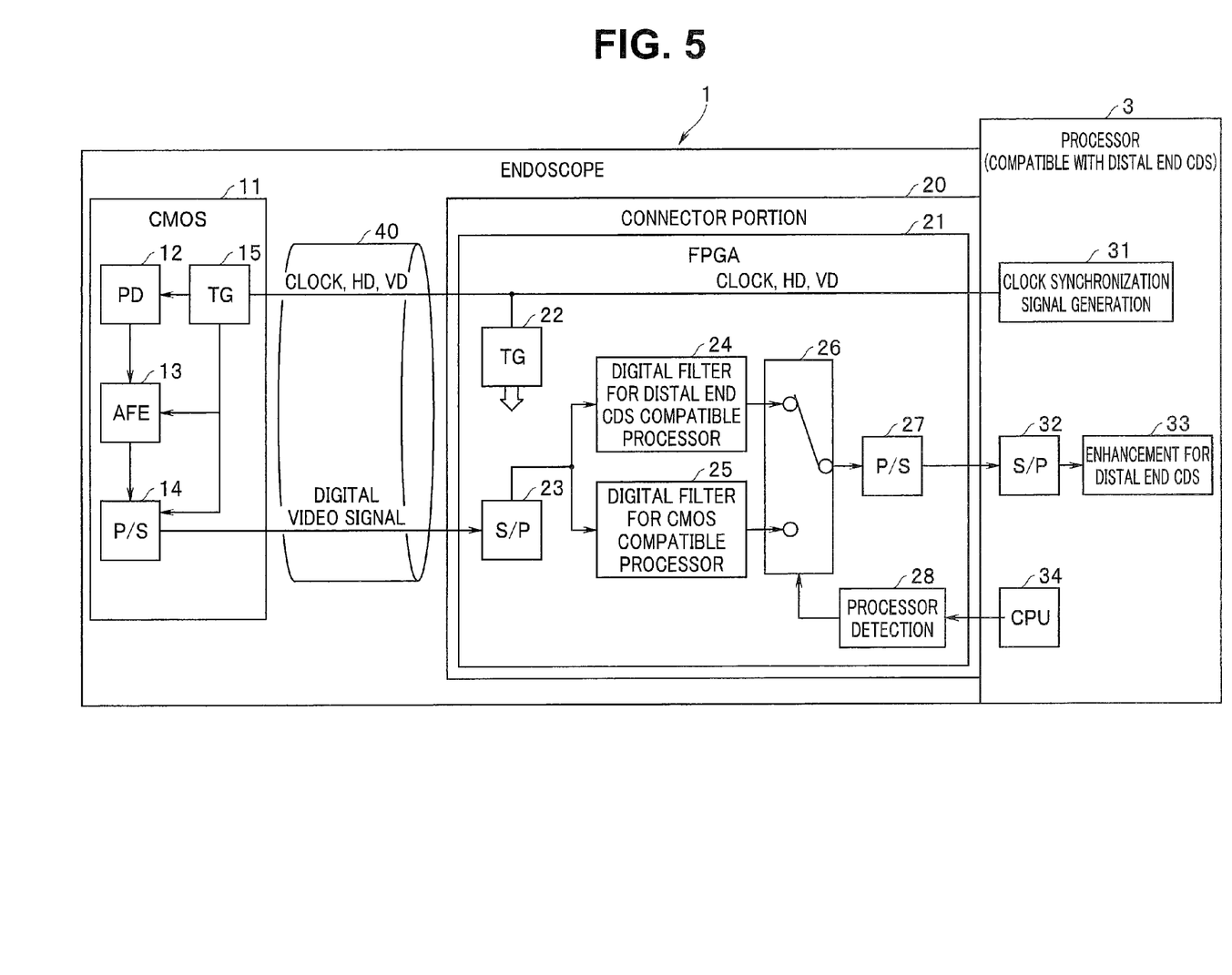
FIG. 5 is a diagram showing a configuration when the endoscope of the first embodiment is connected to the distal end CDS compatible processor.

As shown in FIG. 5, the distal end CDS compatible processor 3 is provided with: the clock synchronization signal generation circuit 31 configured to generate a predetermined clock signal and synchronization signals HD, VD; an S/P conversion circuit 32 configured to perform serial/parallel conversion of a digital image pickup signal, which is a serial signal, outputted from a connected endoscope; the enhancement circuit for distal end CDS 33 connected to the S/P conversion circuit 32; and a CPU 34 configured to control various circuits in the processor 3.

Here, the enhancement circuit for distal end CDS 33 plays a role of enhancing a high-frequency component of an image pickup signal from the endoscope 101 which has been serial/parallel converted by the S/P conversion circuit 32. Details will be described later.

Further, the CPU 34 in the processor 3 plays a role of transmitting ID information specific to the processor 3 (especially, information to the effect that the processor 3 is a distal end CDS compatible processor), which is stored in a memory not shown, to the connected endoscope 1.

On the other hand, the processor detection circuit 28 in the endoscope 1 of the present embodiment is adapted to identify, based on the information from the CPU 34 in the connected processor 3, whether the connected processor is a distal end CDS compatible processor or not.

Note that, though such that has a function of sending out the ID information specific to the processor 3 (the information to the effect that the processor 3 is a distal end CDS compatible processor) to the endoscope 1 is assumed as the processor 3 described above, and the processor detection circuit 28 is assumed to be such that obtains the ID information to identify the classification of the connected processor, the method for identifying a processor is not limited to that.

For example, a classification of the processor 3 may be identified based on predetermined ID information not being received from a connected processor.

More specifically, if such specifications are adopted that, on an assumption that, from a "CMOS compatible processor", ID information specific to the processor, that is, information to the effect that the processor is a CMOS compatible processor is necessarily sent out, and the ID information for identifying a processor is not sent out at all from a distal end CDS compatible processor like the processor 3 as described later, then it is possible to judge that the processor 3 is a distal end CDS compatible processor based on the ID information not being received.

Here, a state example when the endoscope 101 including a CDS processing circuit is connected to the processor 3 will be described with reference to FIG. 8.

As described above, an endoscope has been conventionally known which is configured to perform CDS processing (correlated double sampling processing) for an image pickup signal from an image pickup device at a distal end portion of the endoscope to transmit the image pickup signal after reducing a transmission band.

Figure 8:
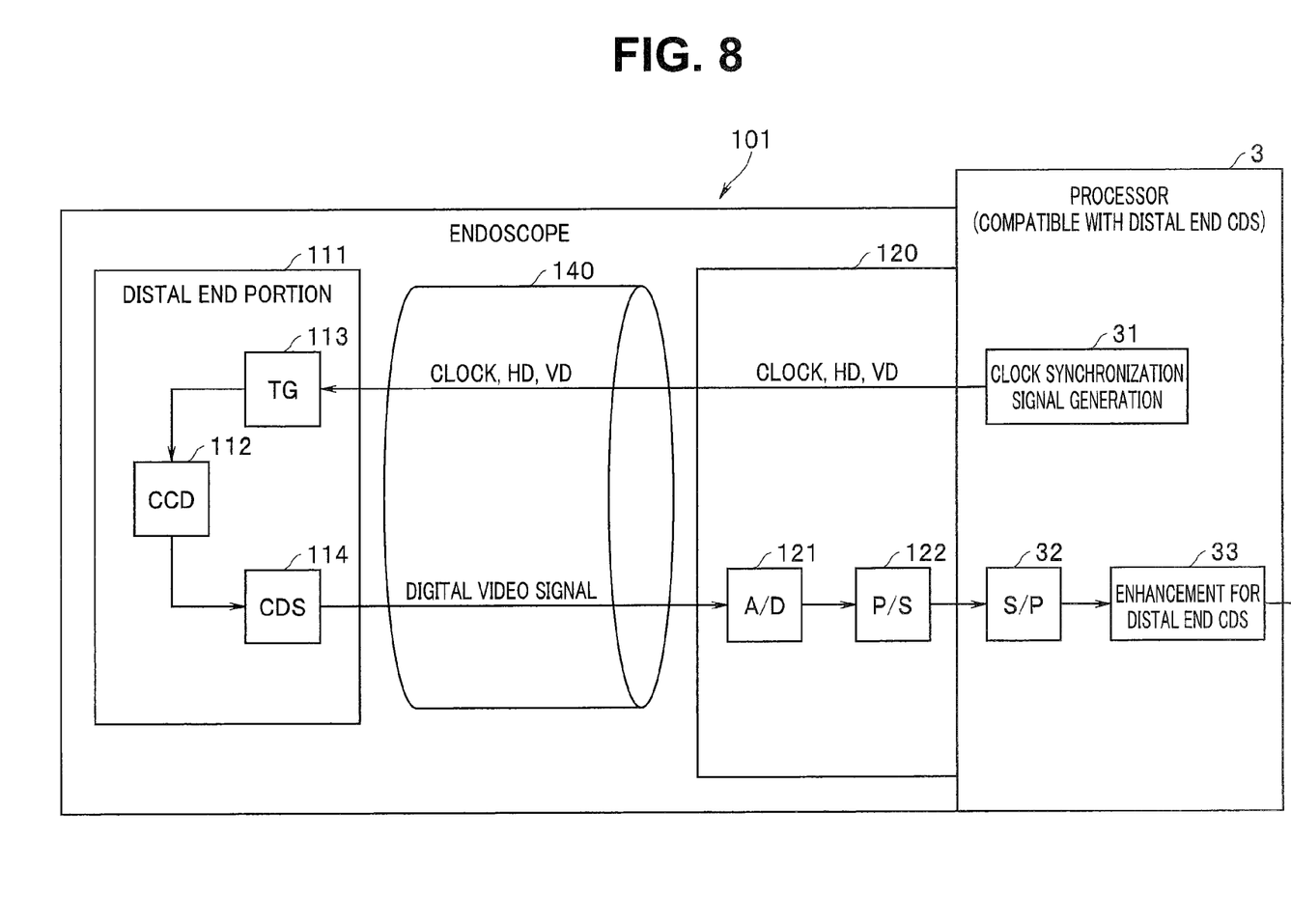
FIG. 8 is a diagram showing a state example when the conventional endoscope is connected to a processor.

More specifically, as shown in FIG. 8, the conventional endoscope 101 is provided with a CCD image sensor 112 configured to pick up an optical image of a subject and output a predetermined analog image pickup signal based on a timing generator 113, as well as a CDS circuit 114 configured to perform correlated double sampling processing for the analog image pickup signal, at a distal end portion 111 of an insertion portion to be inserted into a subject.

Then, the analog image pickup signal for which the correlated double sampling processing has been performed passes through a relatively long cable 140, and, at a connector portion 120, the analog image pickup signal is parallel/serial converted after being A/D converted, and outputted to the processor 3.

On the other hand, in order to make up for frequency deterioration in the cable 140, the processor 3 is provided with the enhancement circuit for distal end CDS 33 configured to send out a clock signal and synchronization signals HD, VD to the endoscope 101 as well as enhancing a high frequency component of the image pickup signal from the endoscope 101 which has been serial/parallel converted by the S/P conversion circuit 32.

Figure 9:
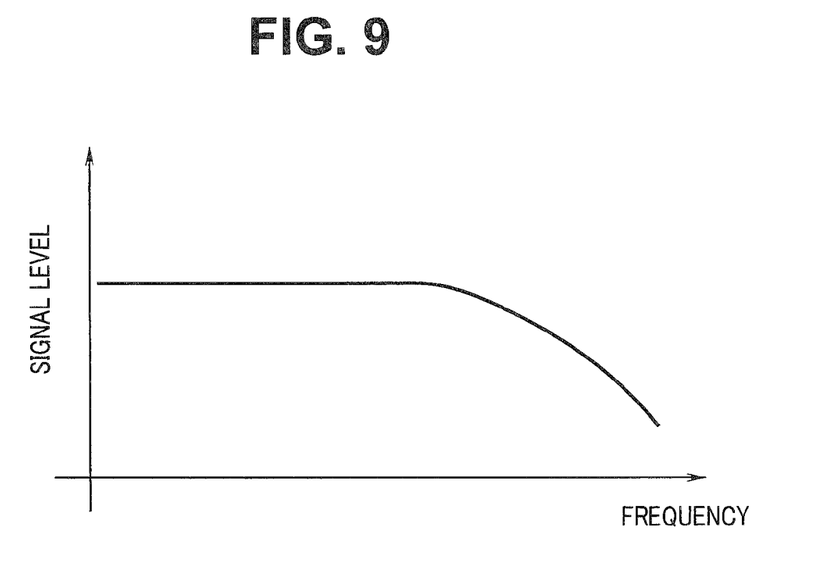
FIG. 9 is a diagram showing an example of transmission signal characteristics of the conventional endoscope.

Here, as described above, in the endoscope 101 of this kind, the cable 140 connecting an image pickup device arranged at the distal end portion 111 (the CCD image sensor 112) and the processor 3 is relatively long. In addition, since a diameter of the cable 140 is restricted in order to realize reduction in a diameter of the insertion portion of the endoscope, a signal output from the CCD image sensor 112 is influenced by physical characteristics of the cable 140, and a high frequency component of the signal easily deteriorates (see FIG. 9).

Figure 10:
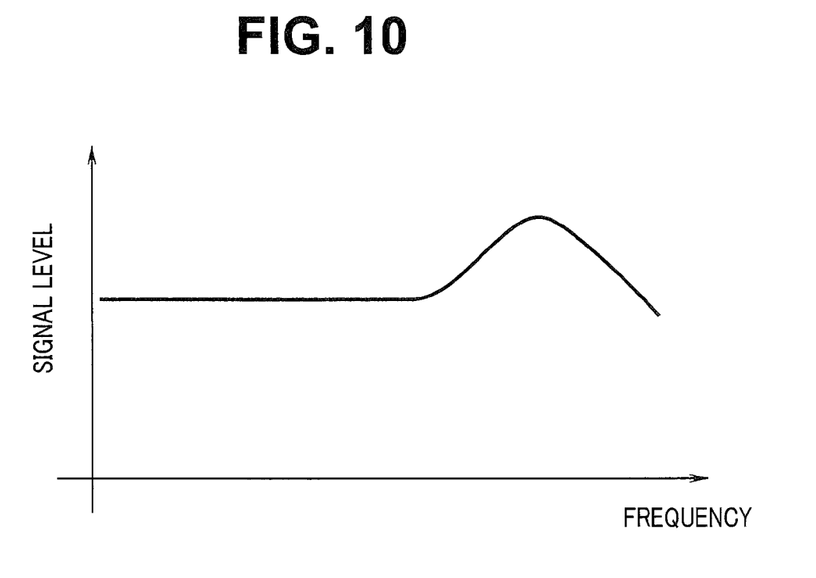
FIG. 10 is a diagram showing an example of signal characteristics of an enhancement circuit for distal end CDS of the distal end CDS compatible processor to which the conventional endoscope is connected.

In view of the situation described above, the enhancement circuit for distal end CDS 33 is adapted to perform correction so as to enhance a high frequency component deteriorated in the cable 140 by the contributing factor described above to perform output (see FIG. 10).

On the other hand, the endoscope 1 of the present embodiment is connectable to the processor 3A in addition to the conventional processor 3 provided with the enhancement circuit for distal end CDS 33.

Figure 4:
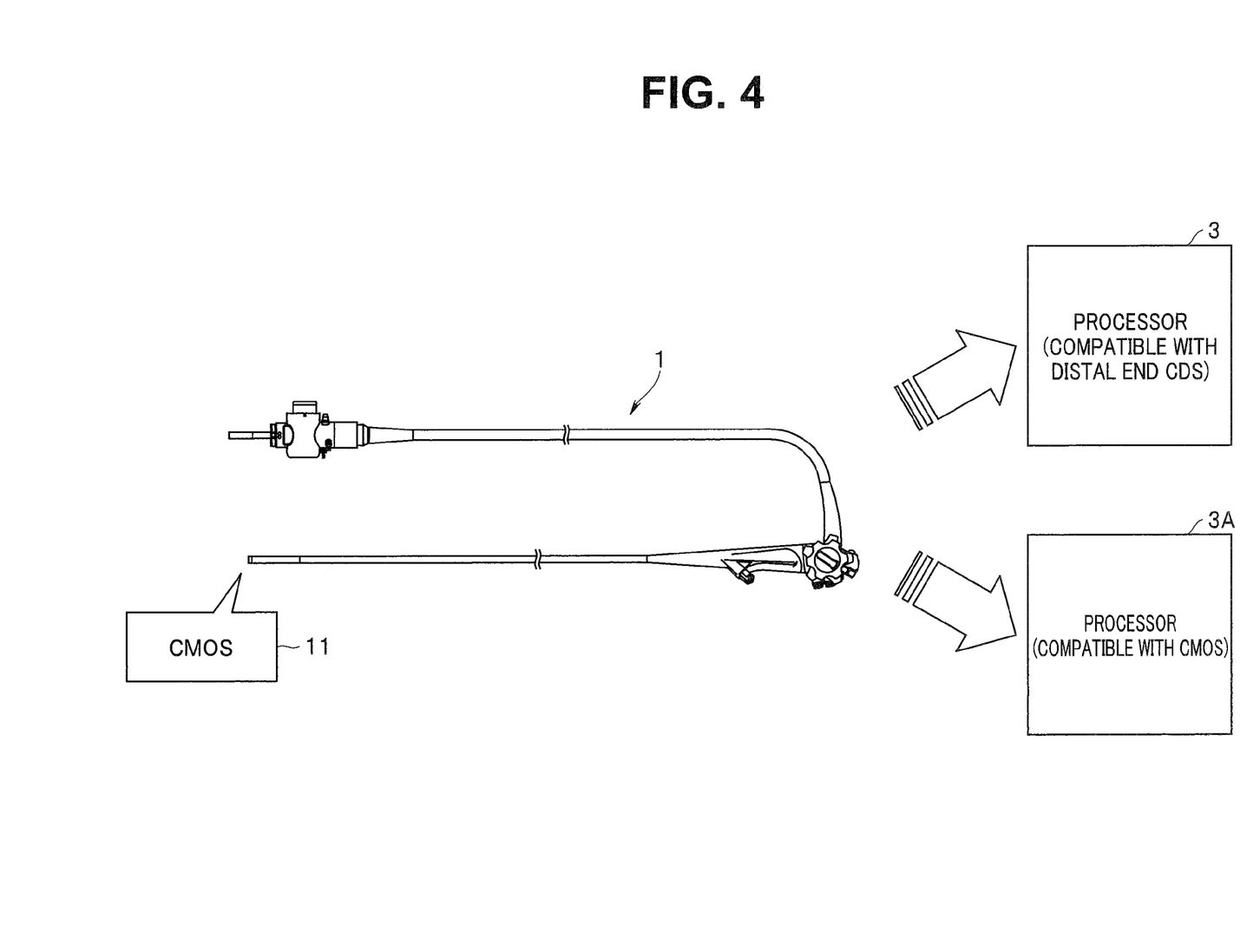
FIG. 4 is a diagram showing a connection relationship among the endoscope of the first embodiment, the distal end CDS compatible processor and a CMOS compatible processor.

FIG. 4 is a diagram showing a connection relationship among the endoscope of the present embodiment, the distal end CDS compatible processor and the CMOS compatible processor.

The processor 3A is provided with a signal processing circuit which assumes that the endoscope 1 mounted with the CMOS image sensor 11 is to be connected.

Here, as described above, transmission of a digital signal is less influenced by physical characteristics of a cable itself in comparison with transmission of an analog signal, from a viewpoint of frequency characteristics, and, therefore, influence of signal deterioration (especially influence of deterioration of a high frequency component) given to image quality is less in the endoscope 1 configured to output a sensor output signal as a digital signal, in comparison with the endoscope 101 adopting a CCD image sensor configured to output a sensor output signal as an analog signal, even in a case of signal transmission with a relatively long cable.

That is, the processor 3A is provided with a signal processing circuit which assumes that an image pickup signal which is less influenced by deterioration of a high frequency component due to the cable 40 is to be inputted.

In other words, the processor 3A is not provided with an enhancement circuit corresponding to the enhancement circuit for distal end CDS 33.

Next, each of operation when the endoscope 1 of the present embodiment is connected to the distal end CDS compatible processor 3 and operation when the endoscope 1 is connected to the CMOS compatible processor 3A will be described.

Figure 6:
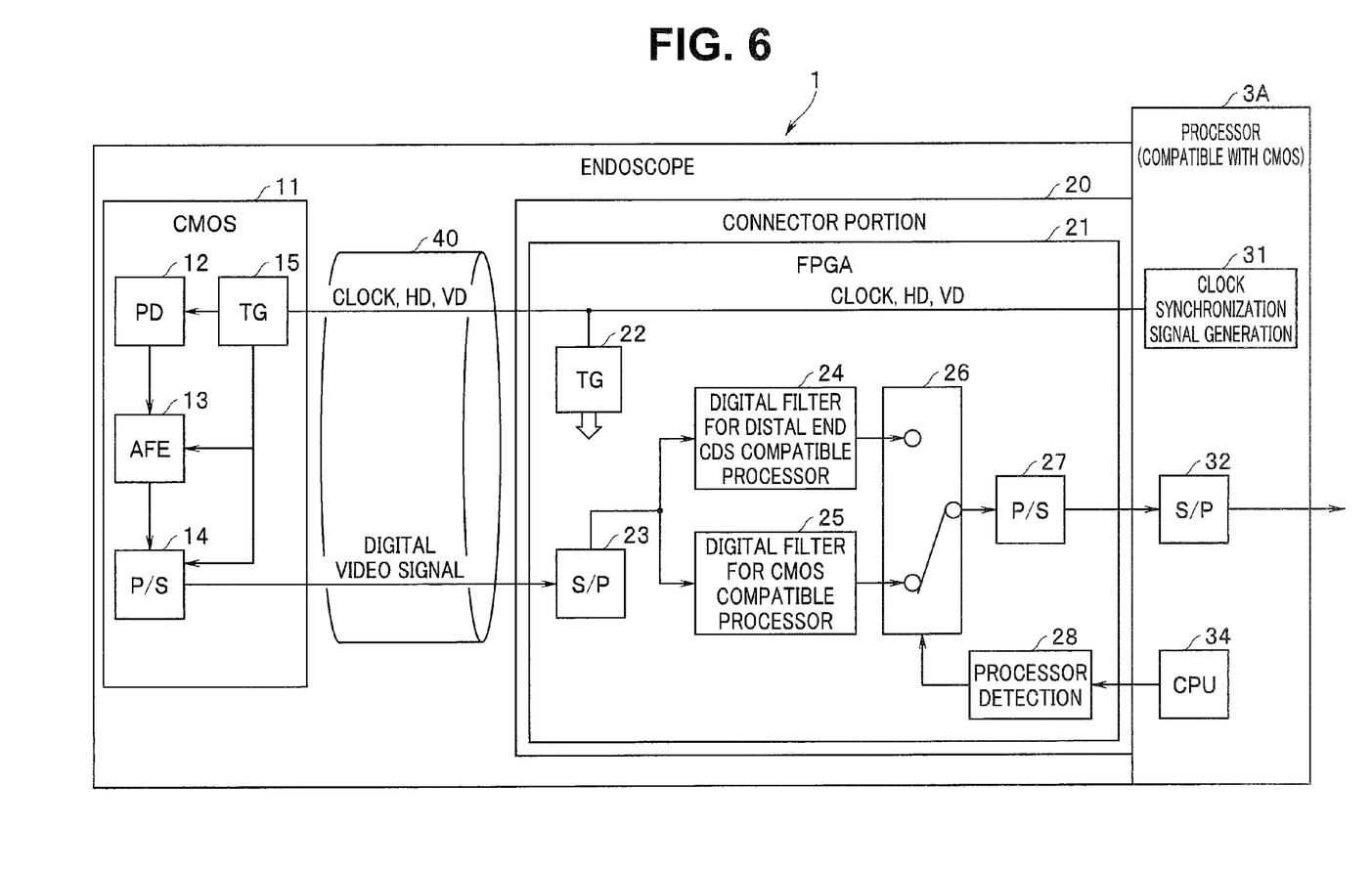
FIG. 6 is a diagram showing a configuration when the endoscope of the first embodiment is connected to the CMOS compatible processor.

FIG. 5 is a diagram showing a configuration when the endoscope of the present embodiment is connected to the distal end CDS compatible processor; and FIG. 6 is a diagram showing a configuration when the endoscope of the present embodiment is connected to the CMOS compatible processor. Furthermore, FIG. 7 is a flowchart showing a digital filter selection process in the endoscope of the present embodiment.

Figure 7:
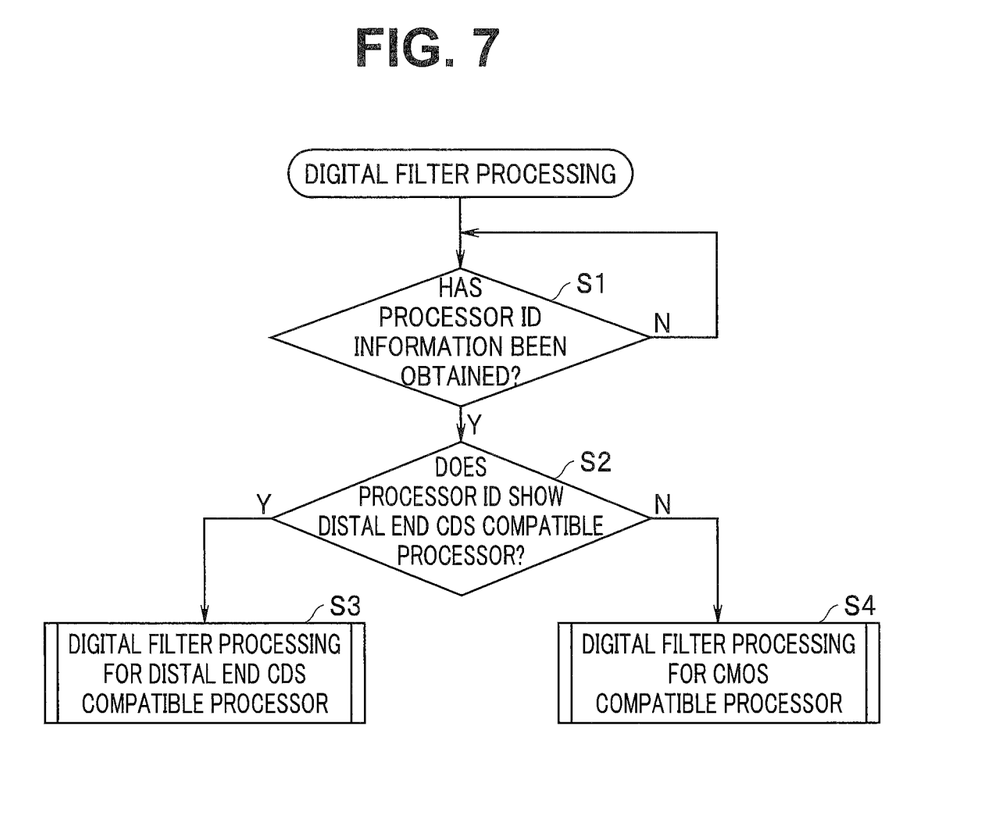
FIG. 7 is a flowchart showing operation of digital filter processing in the endoscope of the first embodiment.

As shown in FIG. 7, first, when the processor detection circuit 28 in the endoscope 1 detects being connected to a predetermined processor, the processor detection circuit 28 obtains predetermined ID information from the CPU 34 (see FIGS. 5 and 6) of the connected processor (step S1).

After that, the processor detection circuit 28 judges whether the connected processor is the distal end CDS compatible processor 3 to which the endoscope 1 is connected or the CMOS compatible processor 3A, based on the ID information obtained at step S1 (step S2).

Note that the processor detection circuit 28 may judge whether the processor 3 is a distal end CDS compatible processor or not based on not receiving ID information as described above.

Then, if the connected processor is the distal end CDS compatible processor 3 (that is, if the connected processor is a processor configured so that the enhancement circuit for distal end CDS 33 works for an image pickup signal), the processor detection circuit 28 performs a process of step S3.

That is, at step S3, the processor detection circuit 28 controls the signal route switching portion 26 to switch a signal route so that an image pickup signal outputted from the P/S circuit 27 passes through the CDS compatible digital filter 24 (see FIG. 5).

Here, as described above, since a digital image pickup signal is outputted from the CMOS image sensor 11, a high frequency component of video based on the image pickup signal does not deteriorate almost at all in a process of transmission by the cable 40. Therefore, if the image pickup signal is inputted to the processor 3 as described above as it is, the high frequency component of the video is enhanced more than necessary.

In the present embodiment, however, the CDS compatible digital filter 24 is configured as the inverse characteristic filter having the characteristics of equalizing the frequency characteristics of the enhancement circuit for distal end CDS 33.

That is, the high frequency component of the image pickup signal outputted from the endoscope 1 is reduced once. Therefore, in the processor 3 to which the image pickup signal has been inputted, appropriate frequency characteristics can be obtained as a result of being offset by the high frequency enhancing operation by the enhancement circuit for distal end CDS 33.

On the other hand, if the connected processor is the CMOS compatible processor 3A, the processor detection circuit 28 performs a process of step S4.

That is, at step S4, the processor detection circuit 28 controls the signal route switching portion 26 to switch the signal route so that an image pickup signal outputted from the P/S circuit 27 passes through the CMOS compatible digital filter 25 (see FIG. 6).

Note that, when it is considered that a high frequency component of video based on a digital image pickup signal outputted from the CMOS image sensor 11 does not deteriorate almost at all in the cable 40, a circuit configuration may be adopted in which characteristics of the CMOS compatible digital filter 25 show substantially flat frequency characteristics.

As described above, according to the present embodiment, it is possible to provide such an endoscope mounted with a CMOS image sensor that, even when the endoscope is connected to a processor provided with a signal processing circuit configured to enhance a high frequency component of an image pickup signal, appropriate image signal processing can be performed in the processor as described above.

Note that, though it is assumed that the FPGA 21 is arranged in the connector portion 20 in the present embodiment, this is not limiting, and the FPGA 21 may be arranged in the operation portion or the like in the endoscope 1.

Further, though a CMOS image sensor is assumed as the image pickup device of the endoscope 1 in the present embodiment, the image pickup device is not limited to a CMOS image sensor, and the invention of the present application can be applied to an endoscope mounted with an image pickup device on a distal end portion of an insertion portion, the image pickup device being capable of generating a digital image pickup signal at a distal end portion of an insertion portion and sending out the digital image pickup signal to a rear circuit portion via the cable 40 as described above.

Next, a second embodiment of the present invention will be described.

Figure 11:
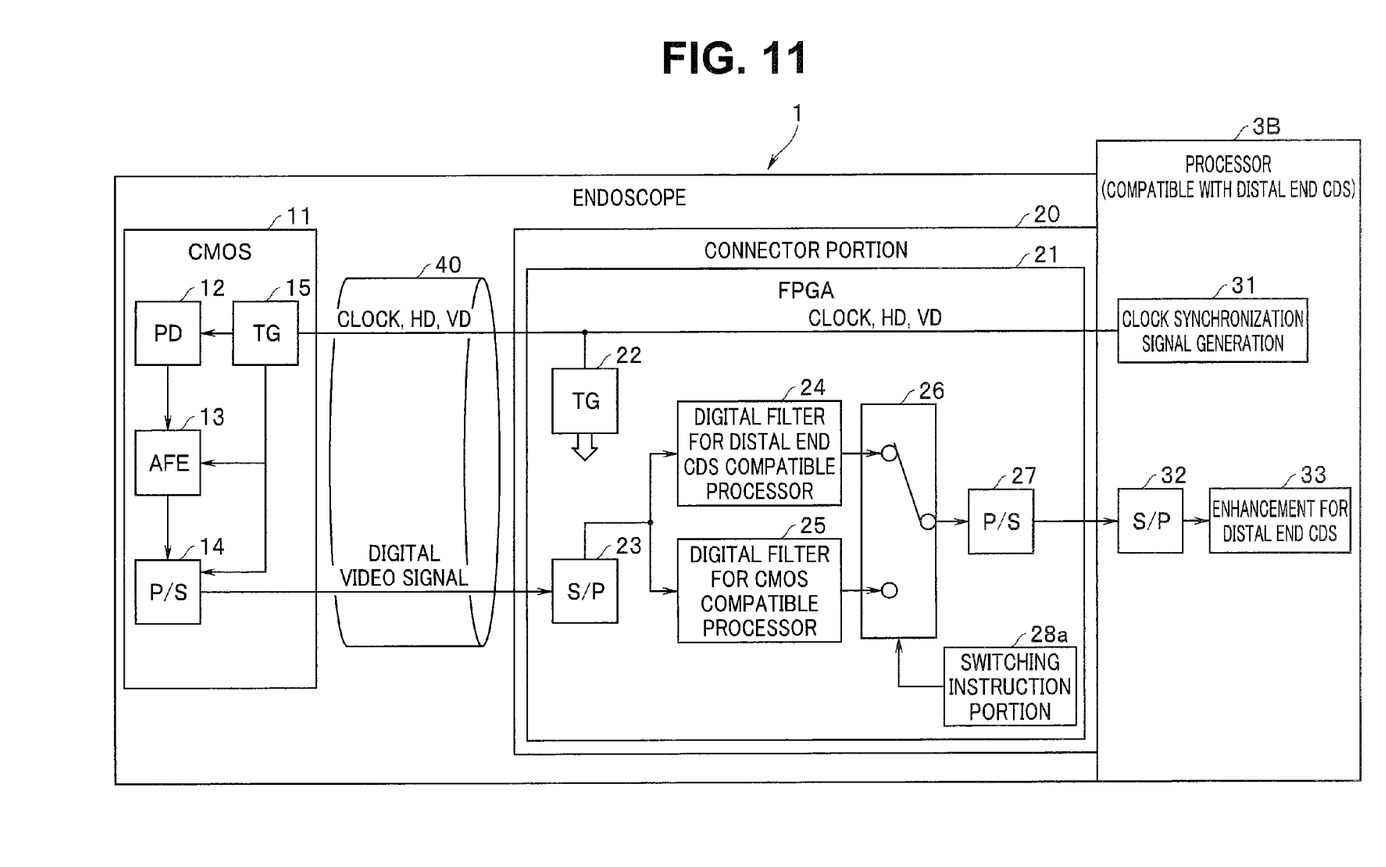
FIG. 11 is a diagram showing a configuration when an endoscope of a second embodiment of the present invention is connected to the distal end CDS compatible processor.
Figure 12:
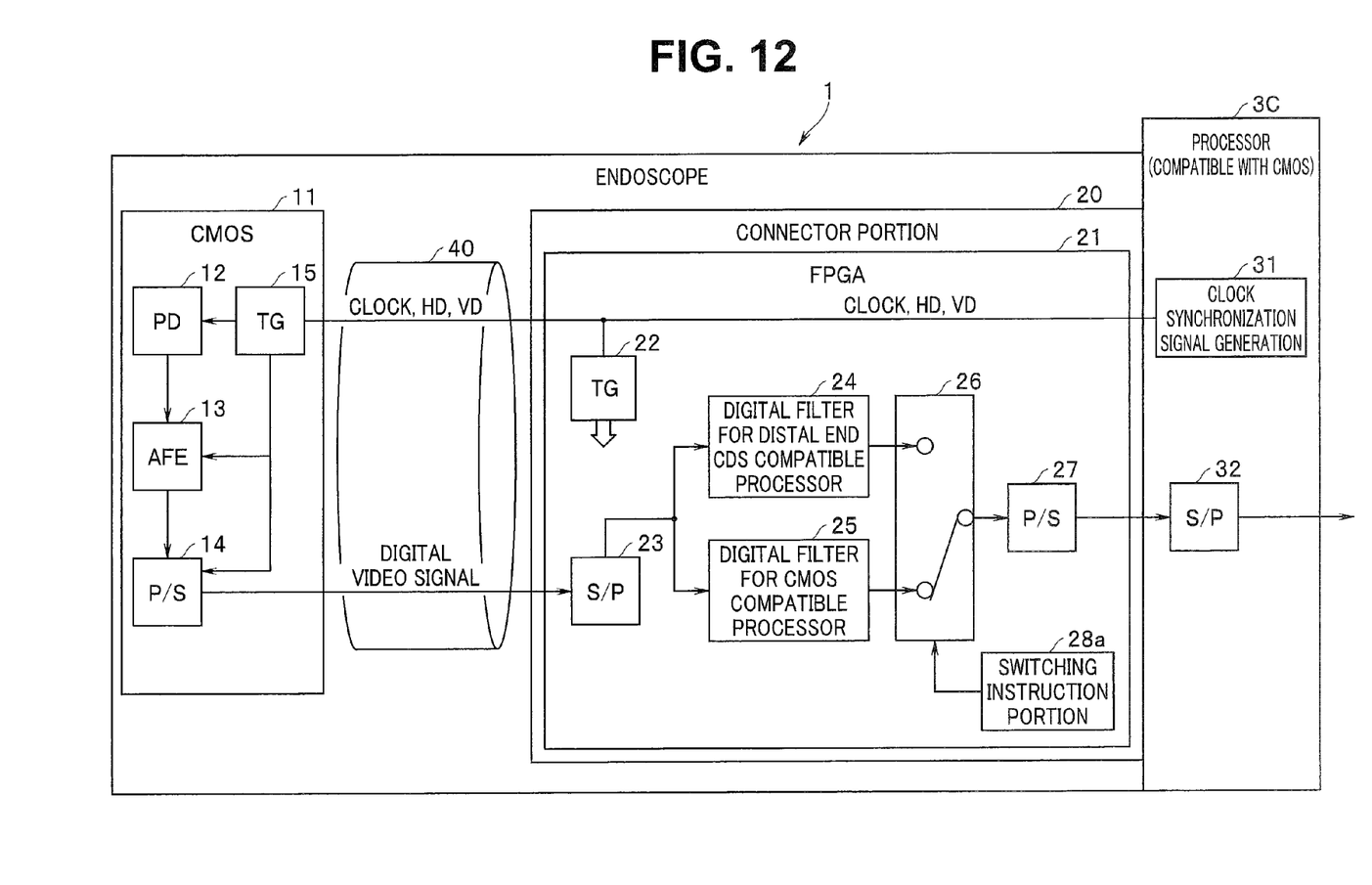
FIG. 12 is a diagram showing a configuration when the endoscope of the second embodiment is connected to the CMOS compatible processor.
Figure 13:
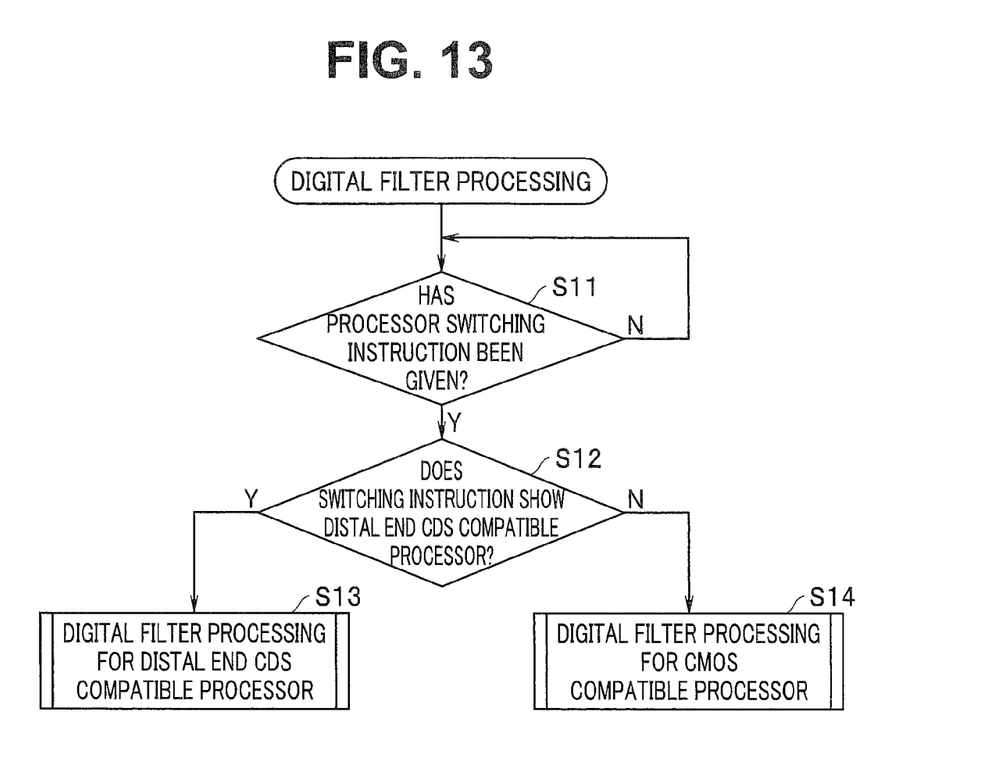
FIG. 13 is a flowchart showing operation of digital filter processing in the endoscope of the second embodiment.

FIG. 11 is a diagram showing a configuration when an endoscope of the second embodiment of the present invention is connected to the distal end CDS compatible processor; and FIG. 12 is a diagram showing a configuration when the endoscope of the second embodiment is connected to the CMOS compatible processor. Furthermore, FIG. 13 is a flowchart showing operation of the digital filter processing in the endoscope of the second embodiment.

A basic configuration of the endoscope system of the present second embodiment is similar to that of the first embodiment, and only a partial configuration inside the FPGA 21 in the connector portion 20 is different. Therefore, only the difference from the first embodiment will be described here, and description of common parts will be omitted.

In the first embodiment described above, the FPGA 21 is provided with the processor detection circuit 28 configured so that the signal route switching portion 26 switches the signal route according to a classification of a processor connected to the endoscope 1 (see FIG. 1). In the second embodiment, however, the FPGA 21 is provided with a switching instruction portion 28a configured to send out a switching instruction signal to switch the signal route to the signal route switching portion 26, instead of the processor detection circuit 28, as shown in FIGS. 11 and 12.

The switching instruction portion 28a sends out the switching instruction signal to the signal route switching portion 26 by an operation or the like not shown (for example, setting by a user). The switching instruction signal is an instruction signal for switching between a first signal route for the digital image pickup signal to pass through the digital filter for distal end CDS compatible processor 24 (an inverse characteristic filter) and a second signal route for the digital image pickup signal to pass through the digital filter for CMOS compatible processor 25 (that is, such a signal route that the digital image pickup signal does not pass through the inverse characteristic filter).

Further, in the present second embodiment, the signal route switching portion 26 is adapted to switch between the first signal route and the second signal route according to the switching instruction signal from the switching instruction portion 28a.

Thus, in the present second embodiment, it is possible to perform the signal route switching described above without the endoscope 1 detecting a classification of a processor connected to the endoscope 1 (a distal end CDS compatible processor 3B (see FIG. 11) or a CMOS compatible processor 3C (see FIG. 12)).

Next, each of operation when the endoscope 1 of the present embodiment is connected to the distal end CDS compatible processor and operation when the endoscope 1 is connected to the CMOS compatible processor will be described.

As shown in FIG. 13, when the switching instruction signal is sent out from the switching instruction portion 28a in the endoscope 1 (step S11), the signal route switching portion 26 switches between the first signal route and the second signal route, based on whether the switching instruction of the switching instruction portion 28a shows the distal end CDS compatible processor 3B or the CMOS compatible processor 3C (step S12).

That is, if the switching instruction signal shows the distal end CDS compatible processor 3B (that is, if the switching instruction signal shows the processor configured so that the enhancement circuit for distal end CDS 33 works for an image pickup signal), the first signal route to pass through the digital filter for distal end CDS compatible processor 24 (the inverse characteristic filter) is selected (step S13).

On the other hand, if the switching instruction signal shows the CMOS compatible processor 3C, the second signal route to pass through the digital filter for CMOS compatible processor 25 is selected (step S14).

Note that, similarly to the first embodiment, when it is considered that a high frequency component of video based on a digital image pickup signal outputted from the CMOS image sensor 11 does not deteriorate almost at all in the cable 40, a circuit configuration may be adopted in which the characteristics of the digital filter for CMOS compatible processor 25 show substantially flat frequency characteristics.

As described above, according to the present embodiment, it is possible to provide such an endoscope mounted with a CMOS image sensor that, even when the endoscope is connected to a processor provided with a signal processing circuit configured to enhance a high frequency component of an image pickup signal, appropriate image signal processing can be performed in the processor, without the endoscope detecting a classification of the connected processor.

Note that the present invention is not limited to the above embodiments as they are, but the components can be modified and embodied within a range not departing from the spirit of the invention at a stage of practicing the invention. Further, various aspects of the invention can be formed by appropriately combining a plurality of components disclosed in the above embodiments. For example, some components may be deleted from all the components shown in the embodiments. Furthermore, components from the different embodiments may be appropriately combined.

Thus, various modifications and applications are, of course, possible within the range not departing from the spirit of the invention.

What is claimed is:

1. An endoscope connectable to a first processor provided with a high frequency component enhancement circuit for performing, for an image pickup signal having an attenuated high frequency component, enhancement correction of the high frequency component and a second processor different from the first processor, the second processor not being provided with the high frequency component enhancement circuit, the endoscope comprising:
   an insertion portion to be inserted into a subject;
   an image pickup device provided at a distal end of the insertion portion and provided with an image pickup portion configured to pick up an optical image of the subject and generate an analog image pickup signal and an A/D converting portion configured to convert the analog image pickup signal to a digital image pickup signal and output the digital image pickup signal;
   a cable having one end connected to the image pickup device, the cable being for transmitting the digital image pickup signal to another end side; and
   an inverse characteristic filter provided at the other end of the cable and having frequency characteristics for equalizing frequency characteristics of the high frequency component enhancement circuit;
   an identifying portion capable of identifying whether the endoscope is connected to the first processor or the second processor; and
   a signal route switching portion configured to switch between a signal route for the digital image pickup signal to pass through the inverse characteristic filter and a signal route for the digital image pickup signal not to pass the inverse characteristic filter according to a result of identification by the identifying portion.

2. The endoscope according to claim 1, wherein the signal route switching portion switches the signal route so that the digital image pickup signal passes through the inverse characteristic filter if the endoscope is connected to the first processor as the result of the identification by the identifying portion, and switches the signal route so that the digital image pickup signal does not pass through the inverse characteristic filter if the endoscope is connected to the second processor.

3. The endoscope connectable to a first processor provided with a high frequency component enhancement circuit for performing, for an image pickup signal having an attenuated high frequency component, enhancement correction of the high frequency component and a second processor different from the first processor, the second processor not being provided with the high frequency component enhancement circuit,
   the endoscope comprising:
   an insertion portion to be inserted into a subject;
   an image pickup device provided at a distal end of the insertion portion and provided with an image pickup portion configured to pick up an optical image of the subject and generate an analog image pickup signal and an A/D converting portion configured to convert the analog image pickup signal to a digital image pickup signal and output the digital image pickup signal;
   a cable having one end connected to the image pickup device, the cable being for transmitting the digital image pickup signal to another end side;
   an inverse characteristic filter provided at the other end of the cable and having frequency characteristics for equalizing frequency characteristics of the high frequency component enhancement circuit;
   a switching instruction portion configured to output a switching instruction signal for switching between a first signal route for the digital image pickup signal to pass through the inverse characteristic filter and a second signal route for the digital image pickup signal not to pass through the inverse characteristic filter; and
   a signal route switching portion configured to switch between the first signal route and the second signal route according to the switching instruction signal from the switching instruction portion.

* * * * *